(12) United States Patent
Pschenitzka

(10) Patent No.: US 8,723,216 B2
(45) Date of Patent: May 13, 2014

(54) METHOD OF TUNING WORK FUNCTION OF METAL NANOSTRUCTURE-BASED TRANSPARENT CONDUCTOR

(75) Inventor: Florian Pschenitzka, San Francisco, CA (US)

(73) Assignee: Cambrios Technologies Corporation, Sunnyvale, CA (US)

( * ) Notice: Subject to any disclaimer, the term of this patent is extended or adjusted under 35 U.S.C. 154(b) by 0 days.

(21) Appl. No.: 13/411,154

(22) Filed: Mar. 2, 2012

(65) Prior Publication Data

US 2012/0223358 A1 Sep. 6, 2012

Related U.S. Application Data

(60) Provisional application No. 61/449,519, filed on Mar. 4, 2011.

(51) Int. Cl.
*H01L 33/02* (2010.01)
*G01N 21/76* (2006.01)
*H01L 33/62* (2010.01)

(52) U.S. Cl.
CPC .............. *G01N 21/763* (2013.01); *H01L 33/62* (2013.01)
USPC .......................................................... 257/99

(58) Field of Classification Search
CPC .............................. H01L 33/02; G01N 21/763
USPC .......................................................... 257/99
See application file for complete search history.

(56) References Cited

U.S. PATENT DOCUMENTS

| | | | |
|---|---|---|---|
| 8,049,333 B2 | 11/2011 | Alden et al. | |
| 8,563,133 B2 * | 10/2013 | Whiteford et al. | 428/402 |
| 2007/0120119 A1 | 5/2007 | Asabe | |
| 2008/0210052 A1 | 9/2008 | Allemand | |
| 2010/0178417 A1 * | 7/2010 | Connor et al. | 427/74 |
| 2010/0307792 A1 * | 12/2010 | Allemand et al. | 174/126.1 |
| 2013/0156938 A1 * | 6/2013 | Geddes et al. | 427/8 |

FOREIGN PATENT DOCUMENTS

WO WO 2010/129604 A1 11/2010

OTHER PUBLICATIONS

Cho et al., "Tuning of Metal Work Function with Organic Carboxylates and Its Application in Top-Emitting Electroluminescent Devices," *Langmuir* 23: 7090-7095, May 24, 2007.

Ganzorig et al., "Fine tuning work function of indium tin oxide by surface molecular design: Enhanced hole injection in organic electroluminescent devices," *Applied Physics Letters* 79(2): 272-274, Jul. 9, 2001.

Gu et al., "Modification of work function of Ti by self-assembled monolayer molecules on $SiO_2/p$-Si," *J Appl Phys* 97: 123710, 2005, 5 pages.

Ha et al., "O-Phenylenediamine Encapsulated Silver Nanoparticles and Their Applications for Organic Light-Emitting Devices," in Silver Nanoparticles, David Pozo Perez (Ed.), ISBN: 978-953-307-028-5, InTech.

(Continued)

*Primary Examiner* — Michael Lebentritt
(74) *Attorney, Agent, or Firm* — Seed IP Law Group PLLC

(57) ABSTRACT

The present disclosure relates to methods for tuning the work function of a metal nanostructure-based conductive film by forming a dipole surface layer on individual metal nanostructures.

23 Claims, 2 Drawing Sheets

(56) References Cited

OTHER PUBLICATIONS

Sun et al., "Crystalline Silver Nanowires by Soft Solution Processing," *Nano Letters* 2(2): 165-168, 2002.

Wu et al., "Surface modification of indium tin oxide by plasma treatment: An effective method to improve the efficiency, brightness, and reliability of organic light emitting devices," *Applied Physics Letters* 70(11): 1348-1350, Mar. 17, 1997.

* cited by examiner

METHOD OF TUNING WORK FUNCTION OF METAL NANOSTRUCTURE-BASED TRANSPARENT CONDUCTOR

CROSS-REFERENCE TO RELATED APPLICATION

This application claims the benefit under 35 U.S.C. §119(e) of U.S. Provisional Patent Application No. 61/449,519, filed Mar. 4, 2011, where this provisional application is incorporated herein by reference in its entirety.

BACKGROUND

1. Technical Field

This disclosure generally relates to tuning the working function of transparent electrode in electroluminescence (EL) devices, in particular, organic light-emitting diodes (OLEDs).

2. Description of the Related Art

An OLED emits light in response to an electric current. FIG. 1 shows a typical OLED (10) formed on a transparent substrate (20). An anode (30) is disposed on the transparent substrate (20) and is also transparent to allow the internally generated light to exit. The light-emitting layer takes the form of an organic emissive stack (40), which is disposed between the anode (30) and a cathode (50). The organic emissive stack (40) includes a thin film of electroluminescent chemical compounds (60) flanked by two charge injection layers (70 and 80, one for electron injection and one for hole injection).

Although indium tin oxide (ITO) is commonly used as the transparent electrode in an OLED, metal nanostructure-based transparent conductors represent an emerging class of transparent electrodes. Unlike the ITO, which is vacuum deposited on a substrate, metal nanostructure-based transparent conductors are formed by coating an ink formulation of metal nanowires on a substrate. The process addresses certain production limitations encountered by the ITO, and is particularly suitable for printing or coating on large area and/or flexible substrates.

The light generation mechanism of the OLED is based on radiative recombination of excitons of electrically excited organic compound(s). As a current of electrons flows through the OLED from the cathode to the anode, electrons are injected into the lowest unoccupied molecular orbital (LUMO) of the organic compound at the cathode and withdrawn from the highest occupied molecular orbital (HOMO) at the anode. The process of withdrawing the electrons from the HOMO may also be described as injecting holes into the HOMO. Electrostatic forces bring the electrons and the holes toward each other and they recombine forming an exciton, an excited state of the electron bound to the hole. The excited state relaxes to the ground state of the electron, accompanied by emission of radiation, the frequency of which is in the visible region (380-800 nm). The frequency of the radiation depends on the difference in energy between the HOMO and LUMO.

In addition to determining the frequencies of the emitted light, the energy levels HOMO and LUMO, as well as those of the electrodes, have significant impact on the efficiency and the performance of the OLED. FIG. 2 shows schematically an energy diagram of an OLED. The energy difference between the anode and HOMO represents an energy barrier ($E_h$) for the hole injection. Similarly, the energy difference between the cathode and LUMO represents an energy barrier ($E_e$) for the electron injection.

Work function of an anode (or cathode) corresponds to the minimum amount of energy needed to remove an electron from the surface of the anode (or cathode). As shown in FIG. 2, increasing the work function of the anode (e.g., to the dashed line) decreases the energy barrier ($E_h$), thereby increasing the efficiency of the hole injection from the anode.

The work function of a surface is strongly affected by the condition of the surface. For example, the work function of ITO can be increased from 4.2 eV to 4.8 eV by oxygen plasma. See, e.g., Wu, C. C. et al. *Appl. Phys. Lett.* 70 (11): 1348 (1997). Changing the work function of a material by absorption of a thin layer of a substance with an electrostatic dipole has also been reported. See, e.g., Gu, D. et al. *J. Appl. Phys.* 97:123710 (2005).

There remains a need to adjust the work function of the metal nanostructure-based transparent conductor in an OLED device.

BRIEF SUMMARY

Provided herein include a method for adjusting work function of a metal nanostructure-based conductive film, the method comprising: providing a plurality of metal nanostructures, each metal nanostructure having an outer surface; and forming a dipole surface layer on the outer surface of the metal nanostructure, wherein the dipole surface layer includes a plurality of dipole ligands.

In various embodiments, forming the dipole surface layer on the outer surface of the metal nanostructure includes: forming an ink composition that comprises the plurality of metal nanostructures and the plurality of dipole ligand, and coating the ink composition on a substrate to provide the conductive film.

In certain embodiments, adjusting work function includes increasing the work function by about 0.8-1.2 eV as compared to a conductive film form of metal nanostructures without a dipole surface layer.

In various embodiments, the dipole ligand is a polar molecule such as a surfactant. In more specific embodiments, an anionic fluorosurfactant is used as the dipole ligand. In an even more specific embodiment, the dipole ligand is lithium carboxylate anionic fluorosurfactant.

Also provide herein is an ink composition that comprises: a plurality of metal nanowires, and a dipole ligand, wherein the dipole ligand is present at about $10^{-6}$ to $10^{-4}$ moles per m$^2$ surface area of the metal nanostructures.

In a further embodiment, the dipole ligand is present at about $10^{-5}$ to $10^{-4}$ moles per m$^2$ surface area of the metal nanostructures.

In various embodiments, the metal nanostructures are silver nanowires.

In certain embodiments, the dipole ligand is an anionic fluorosurfactant. In more specific embodiments, the anionic fluorosurfactant is a lithium carboxylate anionic fluorosurfactant.

In further embodiments, the ink composition may further comprise a surfactant, wherein a weight ratio of the plurality of the metal nanowires and the surfactant is in a range of 560:1 to 5:1.

In other embodiments, the ink composition may further comprise a viscosity modifier, such as hydroxypropyl methylcellulose (HPMC).

A further embodiment provides an OLED device comprising, a cathode, an anode, and an organic emissive stack disposed between the cathode and the anode, wherein the anode includes a conductive film of a plurality of metal nanostructures, each metal nanostructure having an outer surface and a dipole surface layer disposed on the outer surface, and wherein the dipole surface layer includes a plurality of dipole ligands.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been selected solely for ease of recognition in the drawings.

DETAILED DESCRIPTION

Described herein are methods for adjusting work function of nanostructure-based transparent conductor. In particular, the methods are directed to increasing the work function of a metal nanostructure-based transparent conductor (anode) in an OLED by modifying the surface of the metal nanostructures. By increasing the work function of the anode, the energy levels of the organic emissive stack and the anode are better aligned, thereby enhancing the quantum efficiency of the OLED and/or lowering the turn-on voltage. As a result, the overall power efficiency of the device is increased.

Thus, one embodiment provides a method for adjusting work function of a metal nanostructure-based transparent conductor comprising: providing a plurality of metal nanostructures, each metal nanostructure having an outer surface; forming a dipole surface layer on the outer surface of the metal nanostructure, wherein the dipole surface layer includes a plurality of dipole ligands.

As used herein, a "dipole ligand" refers to a molecule or a particle that has a non-uniform distribution of positive and negative charges. The dipole ligand may have a permanent dipole. For example, a polar molecule such as an ionic surfactant has a permanent dipole, which arises from substantially different electronegativity at one part of the molecule (e.g., the polar head of the surfactant) from another part of the molecule (e.g., the lipophilic tail of the surfactant). The dipole ligand may also have an induced dipole (e.g., a polarizable molecule), in which case, the non-uniform distribution of the positive and negative charges are caused by a nearby molecule or particle that has a permanent dipole.

Figure 1:
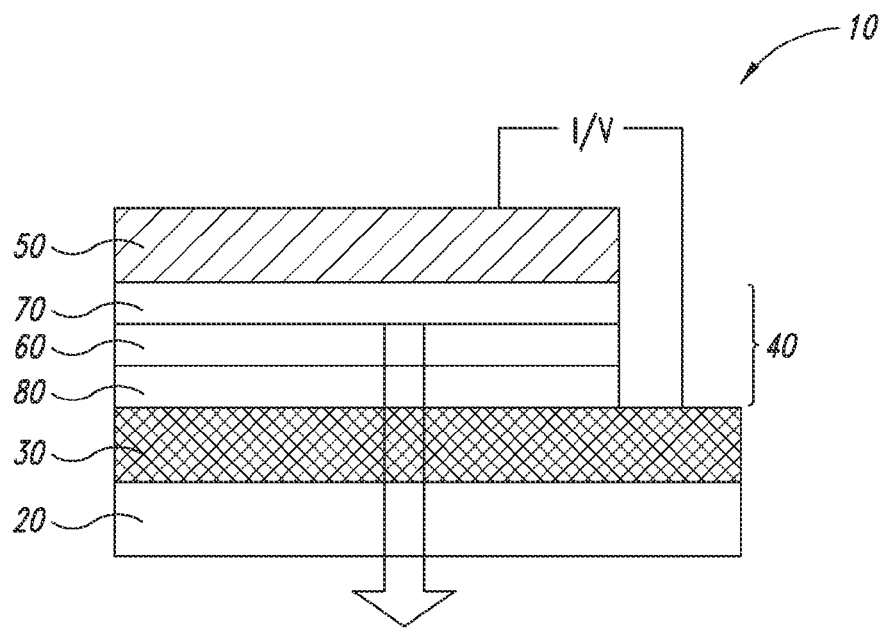
FIG. 1 shows a diagram of an OLED.
Figure 2:
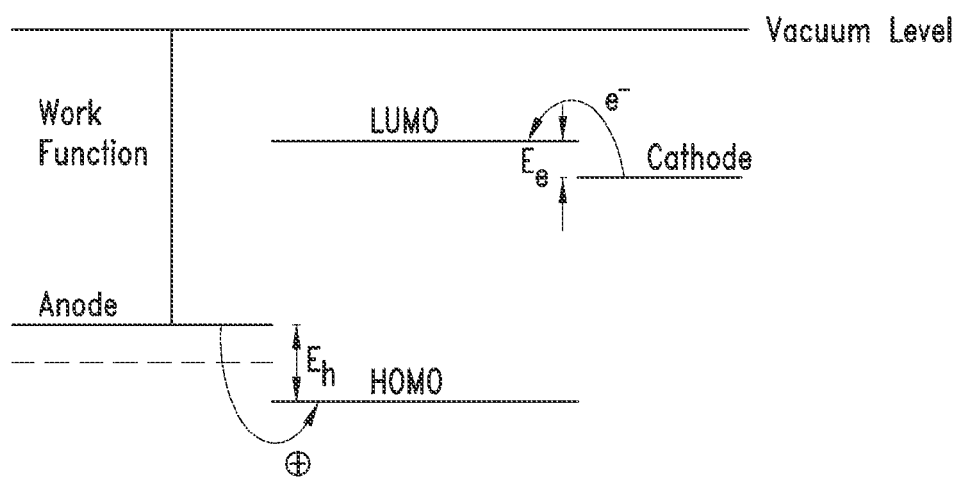
FIG. 2 shows an energy diagram of an OLED.
Figure 3:
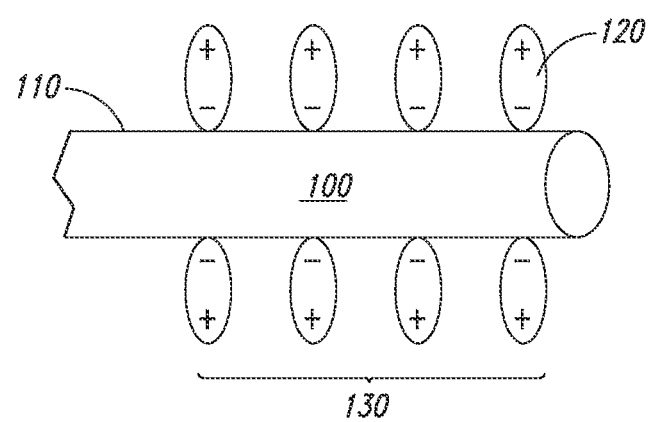
FIG. 3 shows an embodiment according to the present disclosure.

FIG. 3 schematically shows a nanowire (100) with an outer surface (110), on which dipole ligands (120) adsorb. Dipole ligands (120) in the surface region are subjected to orienting forces as a result of the anisotropic force field. Polar molecules (e.g. permanent dipoles) may thus be preferentially oriented in the surface region, while polarizable molecules may be polarized (induced dipoles) and oriented. As schematically shown in FIG. 3, the dipole ligands (100) are oriented in such a way that the negative end of the dipole ligand adsorbs to the surface (110), whereas the positive end of the dipole ligand points away from the surface (110). The preferential orientation causes the dipole ligands to form an array, typically of a single layer of the dipole ligands that are oriented in substantially the same direction. Such an array is called a surface dipole layer (130), with which an electric potential drop is associated. It is believed that the electric potential drop causes the increase of the work function of an anode formed by the metal nanowires.

In an alternative configuration, the dipole ligand may orient in such a way that the positive end of the dipole ligand adsorbs to the surface while the negative end points away from the surface. A surface dipole layer thus formed is associated with an electrical potential increase, which decreases the work function. Such a configuration is beneficial for a cathode, in which a decrease in work function reduces the electron injection barrier.

In certain embodiments, forming the dipole surface layer on the outer surface of the metal nanostructure includes first forming an ink composition that comprises the metal nanostructures and the dipole ligand, followed by coating the ink composition on a substrate to provide a conductive film of interconnecting or networking nanostructures.

The method described herein is therefore compatible with the solution-based approach to forming nanostructure-based conductive film. Advantageously, the dipole ligands adsorb to the outer surface of individual metal nanostructures in the liquid phase, and as the ink composition dries or cures on the substrate, a dipole surface layer is formed on each individual metal nanostructure.

In various embodiments, in the presence of the dipole surface layer, metal nanostructures are capable of forming conductive films in which the work function could increase by about 0.8 eV-1.2 eV as compared to conductive films made of the same metal nanostructures but without the dipole surface layer.

In certain embodiments, the dipole ligand is an ionic surfactant molecule, which can be either an anionic (negatively charged) or cationic (positively charged) molecule. In more specific embodiments, the surfactant molecule is an anionic fluorosurfactant. Non-limiting examples include ZONYL® FSA (lithium carboxylate anionic fluorosurfactant). Other dipole ligands with similar properties as ZONYL® FSA can be used, including, e.g., ZONYL® FSN, ZONYL® FSO, ZONYL® FSH (DuPont Chemicals, Wilmington, Del.), and NOVEC™ (3M, St. Paul, Minn.). The shift in work function is intrinsic to the material depending on the strength of the dipole moment.

The dipole ligand can be added directly into an ink composition that comprises metal nanostructures. It is important that the dipole ligand is in sufficient amount relative to the metal nanostructures to form a dipole surface layer on each metal nanostructure. In various embodiments, the dipole ligand is present at about $10^{-6}$ to $10^{-4}$ moles per m$^2$ surface area of the metal nanostructures. In further embodiments, the dipole ligand is present at about $10^{-5}$ to $10^{-4}$ moles per m$^2$ surface area of the metal nanostructures.

It should be understood, however, that a surfactant is not necessarily a dipole ligand, as defined. While non-ionic surfactants can function as conventional surfactants by adsorbing on the nanostructures by static interaction (as opposed to ionic interaction), they may not be capable of forming an array or monolayer. Even ionic surfactants, unless reaching a critical concentration threshold in the ink composition, may not be capable of forming an array or monolayer. Thus, one embodiment provides an ink composition that comprises a plurality of silver nanowires, a surfactant, a viscosity modifier, and a dipole ligand, wherein the dipole ligand is present at about $10^{-6}$ to $10^{-4}$ moles per m$^2$ surface area of the metal nanostructures. In further embodiments, the dipole ligand is present at about $10^{-5}$ to $10^{-4}$ moles per m$^2$ surface area of the metal nanostructures.

In one specific embodiment, by formulating ZONYL® FSA and silver nanowires into an ink composition, followed by coating the ink composition on a substrate to form a conductive film, the work function of the conductive film increases from a range of about 4.5 eV-4.7 eV (without FSA) to a range of about 5.2 eV-5.4 eV.

The conductive film described herein is suitable as an anode in an OLED device. It can be expected that the increase in work function in the film would increase the efficiency of the OLED device. Thus, one embodiment provides an OLED device comprising, a cathode, an anode, and an organic emissive stack disposed between the cathode and the anode, wherein the anode includes a conductive film of a plurality of metal nanostructures, each metal nanostructure having an outer surface and a dipole surface layer disposed on the outer surface, and wherein the dipole surface layer includes a plurality of dipole ligands.

In various embodiments, the dipole ligands are present at $10^{-6}$ to $10^{-4}$ moles per m$^2$ surface area of the metal nanostructures. In further embodiments, the dipole ligand is present at about $10^{-5}$ to $10^{-4}$ moles per m$^2$ surface area of the metal nanostructures. In further embodiments, the dipole ligands are anionic surfactants. In further embodiments, the anode has a work function of 5.2-5.7 eV.

The various components of the conductive film are further described in more detail below.

Metal Nanostructures

As used herein, "metal nanostructures" or "nanostructures" generally refer to electrically conductive nano-sized structures, at least one dimension of which is less than 500 nm, more preferably, less than 250 nm, 100 nm, 50 nm or 25 nm.

The nanostructures can be of any shape or geometry. In certain embodiments, the nanostructures are isotropically shaped (i.e., aspect ratio=1). Typical isotropic nanostructures include nanoparticles. In preferred embodiments, the nanostructures are anisotropically shaped (i.e., aspect ratio≠1). As used herein, "aspect ratio" refers to the ratio between the length and the width (or diameter) of the nanostructure. The anisotropic nanostructure typically has a longitudinal axis along its length. Exemplary anisotropic nanostructures include nanowires and nanotubes, as defined herein.

The nanostructures can be solid or hollow. Solid nanostructures include, for example, nanoparticles and nanowires. "Nanowires" thus refers to solid anisotropic nanostructures. Typically, each nanowire has an aspect ratio (length:diameter) of greater than 10, preferably greater than 50, and more preferably greater than 100. Typically, the nanowires are more than 500 nm, more than 1 µm, or more than 10 µm long.

Hollow nanostructures include, for example, nanotubes. Typically, the nanotube has an aspect ratio (length:diameter) of greater than 10, preferably greater than 50, and more preferably greater than 100. Typically, the nanotubes are more than 500 nm, more than 1 µm, or more than 10 µm in length.

The metal nanostructures can be formed of any electrically conductive metallic material. The metallic material can be an elemental metal (e.g., transition metals) or a metal compound (e.g., metal oxide). The metallic material can also be a bimetallic material or a metal alloy, which comprises two or more types of metal. Suitable metals include, but are not limited to, silver, gold, copper, nickel, gold-plated silver, platinum and palladium.

Conductive Film

In general, a conductive film is typically in a multi-film configuration, and at least includes a nanostructure layer coated on a substrate. The nanostructure layer is formed by depositing an ink composition (also referred to as "coating composition") comprising a liquid carrier and a plurality of metal nanostructures on the substrate.

The nanostructure layer or film comprises nanostructures that are randomly distributed and interconnect with one another. As the number of the nanostructures reaches the percolation threshold, the thin film is electrically conductive. Other non-volatile components of the ink composition, including, for example, one or more binders, surfactants and additional viscosity modifiers, may form part of the conductive film.

The liquid carrier for the dispersion may be water, an alcohol, a ketone or a combination thereof. Exemplary alcohols may include isopropanol (IPA), ethanol, diacetone alcohol (DAA) or a combination of IPA and DAA. Exemplary ketones may include methyl ethyl ketone (MEK) and methyl propyl ketone (MPK). The surfactants serve to reduce aggregation of the nanostructures.

Representative examples of suitable surfactants include fluorosurfactants such as ZONYL® surfactants, including ZONYL® FSN, ZONYL® FSO, ZONYL® FSA, ZONYL® FSH (DuPont Chemicals, Wilmington, Del.), and NOVEC™ (3M, St. Paul, Minn.). Other exemplary surfactants include non-ionic surfactants based on alkylphenol ethoxylates. Preferred surfactants include, for example, octylphenol ethoxylates such as TRITON™ (×100, ×114, ×45), and nonylphenol ethoxylates such as TERGITOL™ (Dow Chemical Company, Midland Mich.). Further exemplary non-ionic surfactants include acetylenic-based surfactants such as DYNOL® (604, 607) (Air Products and Chemicals, Inc., Allentown, Pa.) and n-dodecyl β-D-maltoside.

In certain embodiments, the surfactant may be the same as the dipole ligand. In other embodiments, the surfactant may be different from the dipole ligand and co-exist with the dipole ligand in the ink composition.

The binder acts as a viscosity modifier in the ink composition and may affect the rheology of the same during the coating process. The binder also helps to immobilize the nanostructures on a substrate. Examples of suitable binders include hydroxypropyl methylcellulose (HPMC), methyl cellulose, xanthan gum, polyvinyl alcohol, carboxy methyl cellulose, and hydroxy ethyl cellulose.

In particular embodiments, the weight ratio of the surfactant to the binder in the coating solution is preferably in the range of about 80:1 to about 0.01:1; the weight ratio of the binder to the conductive nanostructures is preferably in the range of about 5:1 to about 0.000625:1; and the weight ratio of the conductive nanostructures to the surfactant is preferably in the range of about 560:1 to about 5:1. The ratios of components of the coating solution may be modified depending on the substrate and the method of application used. A preferred viscosity range for the coating solution is between about 1 and 100 cP.

The electrical conductivity of the conductive film is often measured by "sheet resistance," which is represented by Ohms/square (or "ohms/sq"). The sheet resistance is a function of at least the surface loading density, the size/shapes of the nanostructures, and the intrinsic electrical property of the nanostructure constituents. As used herein, a thin film is considered conductive if it has a sheet resistance of no higher than $10^8$ ohms/sq. Preferably, the sheet resistance is no higher than $10^4$ ohms/sq, 3,000 ohms/sq, 1,000 ohms/sq, 350 ohms/sq, or 100 ohms/sq. Typically, the sheet resistance of a conductive network formed by metal nanostructures is in the range of from 10 ohms/sq to 1000 ohms/sq, from 100 ohms/sq to 750 ohms/sq, 50 ohms/sq to 200 ohms/sq, from 100 ohms/sq to 500 ohms/sq, from 100 ohms/sq to 250 ohms/sq, 10 ohms/sq to 200 ohms/sq, from 10 ohms/sq to 50 ohms/sq, or from 1 ohms/sq to 10 ohms/sq. For the opto-electrical devices described herein, the sheet resistance is typically less than 1000 ohms/sq, less than 500 ohms/sq, less than 100 ohms/sq, less than 50 ohms/square, less than 20 ohms/square, or less than 10 ohms/square.

Optically, the nanostructure-based transparent conductors have high light transmission in the visible region (400 nm-700 nm). Typically, the transparent conductor is considered optically clear when the light transmission is more than 70%, or more typically more than 85% in the visible region. More preferably, the light transmission is more than 90%, more than 93%, or more than 95%. As used herein, unless specified otherwise, a conductive film is optically transparent (e.g., more than 70% in transmission). Thus, transparent conductor; transparent conductive film, layer or coating; conductive film, layer or coating; and transparent electrode are used interchangeably.

Substrate

The substrate supports the nanostructure layer. In certain embodiments, the substrate is the support on which the ink composition is directly coated to form the nanostructure film, as defined herein. In other embodiments, an intermediate layer (i.e., an undercoat) is coated on the substrate before the ink composition is coated.

The substrate can be rigid or flexible. Examples of rigid substrates include glass, polycarbonates, acrylics, and the like. Examples of flexible substrates include, but are not limited to: polyesters (e.g., polyethylene terephthalate (PET), polyester naphthalate, and polycarbonate), polyolefins (e.g., linear, branched, and cyclic polyolefins), polyvinyls (e.g., polyvinyl chloride, polyvinylidene chloride, polyvinyl acetals, polystyrene, polyacrylates, and the like), cellulose ester bases (e.g., cellulose triacetate, and cellulose acetate), polysulphones such as polyethersulphone, polyimides, silicones, and other conventional polymeric films.

EXAMPLES

Example 1

Synthesis of Silver Nanowires

Silver nanowires were synthesized by the reduction of silver nitrate dissolved in ethylene glycol in the presence of poly(vinyl pyrrolidone) (PVP) following the "polyol" method described in, e.g., Y. Sun, B. Gates, B. Mayers, & Y. Xia, "Crystalline silver nanowires by soft solution processing," *Nanoletters* 2 (2):165-168, 2002. A modified polyol method, described in co-pending and co-owned U.S. patent application Ser. No. 11/766,552, produces more uniform silver nanowires at higher yields than does the conventional "polyol" method. This application is incorporated by reference herein in its entirety. Resulting nanowires primarily had lengths from about 13 μm to about 17 μm and diameters from about 25-45 nm.

Example 2

Preparation of Coating Composition of Metal Nanostructures

A standard coating composition for depositing metal nanowires comprises, by weight, from 0.0025% to 0.1% surfactant (e.g., a preferred range is from 0.0025% to 0.05% for the non-ionic surfactant ZONYL® FSO-100), from 0.02% to 4% viscosity modifier (e.g., a preferred range is 0.02% to 0.5% for hydroxypropyl methylcellulose (HPMC), from 94.5% to 99.0% solvent, and from 0.05% to 1.4% metal nanowires. This standard coating solution was used to form a reference film (S1), i.e., one without any dipole ligand.

To prepare coating compositions that include a dipole ligand, ZONYL® FSA was added to the standard coating composition. The silver nanowire:FSA ratio (by weight) was 1:0.7. This dispersion was used to make films for samples S2 and S3 of Example 4. The weight ratio of the silver nanowires and FSA can also be 1:0.1 to 1:1.

The coating composition can be prepared based on a desired concentration of the nanowires, which is an index of the loading density of the final conductive film formed on the substrate.

The coating composition can be deposited on a substrate according to, for example, the methods described in co-pending U.S. patent application Ser. No. 11/504,822.

As understood by one skilled in the art, other deposition techniques can be employed, e.g., sedimentation flow metered by a narrow channel, die flow, flow on an incline, slit coating, gravure coating, microgravure coating, bead coating, dip coating, slot die coating, and the like. Printing techniques can also be used to directly print an ink composition onto a substrate with or without a pattern. For example, inkjet, flexoprinting and screen printing can be employed. It is further understood that the viscosity and shear behavior of the fluid as well as the interactions between the nanowires may affect the distribution and interconnectivity of the nanowires deposited.

Example 3

Work Function Measurement

Work function may be measured by an absolute scan with tip tracking The absolute scan is a scan of approximate dimensions of 6×6 cm$^2$ conducted with a 2 mm diameter Kelvin probe tip. The tip Work Function (WF) has been determined with reference to a pristine gold surface, the work function of which is 5.10 eV.

There are two reasons for performing an absolute scan with tip tracking. The absolute nature of the data allows for comparison with third party measurements. Secondly, the homogeneity of the surface is probed using a constant tip to sample spacing, and is much less sensitive to stray capacitance effects.

The scan may be performed at a constant tip to sample spacing, i.e., tracking, to ensure accurate comparison with the same tip on different samples. Both samples S2 and S3 were measured with Kelvin probe.

In addition, the work function was also determined using an AC-2 Photoelectron Spectrometer (manufactured by Riken Keiki). Sample S4 was analyzed using this method.

Example 4

Work Functions of Nanostructure-Based Conductive Films

Three samples of conductive films were prepared (S1-S3) according to the method described in Example 2. Each sample was 15×15 mm$^2$. The samples were affixed to the sample holder with a conductive tape. S1 did not contain any FSA (dipole ligand) and was used as reference.

For all the samples, the work function data has standard deviations in the 20-100 meV range, which is consistent with macroscopic work function measurements on real surfaces, i.e., surfaces that contain modest inhomogeneity such as scratches. In all the samples, the surfaces were well prepared, i.e., clean and free from fingerprints. The surfaces were further protected by lint-free tissue. As a comparison, for pristine surfaces, the standard deviation was expected to be less than 20 meV.

As the KP tip is macroscopic (2 mm in diameter), artifacts less than this dimension cannot be resolved, i.e., the smallest real feature was 2 mm.

The work function data of these samples are shown in Table 1 below. The data are the mean WF across the whole scan area (e.g., 8×8 mm$^2$) and the standard deviation. These two values serve to differentiate between a homogeneous surface and one exhibiting significant artifacts. The work function data are smoothed.

As a comparison, conductive films (e.g., S1) formed of metal nanostructures without a dipole surface layer typically have work functions in the range of 4.5-4.7 eV. As shown, compared to S1, the work function of S2-S3 increased by about 0.8-1.2 eV. In addition, as demonstrated by the low standard deviation, the work function distribution on a given conducive film is substantially uniform.

TABLE 1

| Samples | Work Function (eV) | Standard Deviation (eV) |
|---|---|---|
| S1 | 4.5-4.7 | |
| S2 | 5.707 | 0.018 |
| S3 | 5.540 | 0.085 |

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for adjusting work function of a metal nanostructure-based conductive film, the method comprising:
   providing a plurality of metal nanostructures, each metal nanostructure having an outer surface; and
   forming a dipole surface layer on the outer surface of the metal nanostructure, wherein the dipole surface layer includes a plurality of dipole ligands, and wherein the dipole ligands are present at about $10^{-6}$ to $10^{-4}$ moles per m$^2$ surface area of the metal nanostructures.

2. The method of claim 1 wherein forming the dipole surface layer on the outer surface of the metal nanostructure includes:
   forming an ink composition that comprises the plurality of metal nanostructures and the plurality of dipole ligand, and
   coating the ink composition on a substrate to provide the conductive film.

3. The method of claim 1, wherein adjusting work function includes increasing the work function by about 0.8-1.2 eV as compared to a conductive film form of metal nanostructures without a dipole surface layer.

4. The method of claim 1, wherein the dipole ligand is a polar molecule.

5. The method of claim 4 wherein the polar molecule is a surfactant.

6. The method of claim 5 wherein the surfactant is an anionic fluorosurfactant.

7. The method of claim 1 wherein the dipole ligand is lithium carboxylate anionic fluorosurfactant.

8. An ink composition comprising:
   a plurality of metal nanowires, and
   a plurality of dipole ligands, wherein the dipole ligands are present at about $10^{-6}$ to $10^{-4}$ moles per m$^2$ surface area of the metal nanostructures.

9. The ink composition of claim 8 wherein the dipole ligands are present at about $10^{-5}$ to $10^{-4}$ moles per m$^2$ surface area of the metal nanostructures.

10. The ink composition of claim 8 wherein the metal nanostructures are silver nanowires.

11. The ink composition of claim 8 wherein the dipole ligand is an anionic fluorosurfactant.

12. The ink composition of claim 11 wherein the anionic fluorosurfactant is a lithium carboxylate anionic fluorosurfactant.

13. The ink composition of claim 8, further comprising: a surfactant, wherein a weight ratio of the plurality of the metal nanowires and the surfactant is in a range of 560:1 to 5:1.

14. The ink composition of claim 8, further comprising a viscosity modifier.

15. The ink composition of claim 14 wherein the viscosity modifier is HPMC.

16. An organic light emitting diode (OLED) device comprising:
   a cathode,
   an anode, and
   an organic emissive stack disposed between the cathode and the anode,
   wherein the anode includes a conductive film of a plurality of metal nanostructures, each metal nanostructure having an outer surface and a dipole surface layer disposed on the outer surface, and wherein the dipole surface layer includes a plurality of dipole ligands, and wherein the dipole ligands are present at about $10^{-6}$ to $10^{-4}$ moles per m$^2$ surface area of the metal nanostructures.

17. The OLED device of claim 16, wherein the dipole ligands are present at $10^{-5}$ to $10^{-4}$ moles per m$^2$ surface area of the metal nanostructures.

18. The OLED device of claim 16, wherein the dipole ligands are anionic surfactants.

19. The OLED device of claim 16, wherein the anode has a work function of 5.2-5.7 eV.

20. A method for adjusting work function of a metal nanostructure-based conductive film, the method comprising:
   providing a plurality of metal nanostructures, each metal nanostructure having an outer surface; and
   forming a dipole surface layer on the outer surface of the metal nanostructure, wherein the dipole surface layer includes a plurality of dipole ligands, wherein adjusting work function includes increasing the work function by about 0.8-1.2 eV as compared to a conductive film form of metal nanostructures without a dipole surface layer.

21. The method of claim 20 wherein the dipole ligand is a fluorosurfactant.

22. A transparent electrode comprising: a conductive film having a plurality of metal nanostructures, each metal nanostructure having an outer surface and a dipole surface layer disposed on the outer surface, wherein the dipole surface layer includes a plurality of dipole ligands and wherein the transparent electrode has a work function of 5.2-5.7 eV.

23. An organic light emitting diode (OLED) device comprising the transparent electrode of claim 22.

* * * * *